(12) United States Patent
Ryan

(10) Patent No.: US 6,280,441 B1
(45) Date of Patent: *Aug. 28, 2001

(54) APPARATUS AND METHOD FOR RF LESIONING

(75) Inventor: Thomas Patrick Ryan, Fort Collins, CO (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/990,377

(22) Filed: Dec. 15, 1997

(51) Int. Cl.⁷ .................................................. A61B 17/36
(52) U.S. Cl. .............................. 606/45; 600/373; 606/41
(58) Field of Search .................................. 606/45, 41, 48; 607/99, 101, 154; 600/373

(56) References Cited

U.S. PATENT DOCUMENTS

| | | |
|---|---|---|
| 4,010,758 | 3/1977 | Rockland et al. . |
| 4,637,392 | 1/1987 | Sorochenko . |
| 4,800,395 | 1/1989 | Balzano et al. . |
| 4,945,912 | 8/1990 | Langberg . |
| 5,047,026 | 9/1991 | Rydell . |
| 5,047,027 | 9/1991 | Rydell . |
| 5,100,423 | 3/1992 | Fearnot . |
| 5,226,890 | 7/1993 | Ianniruberto et al. . |
| 5,334,193 | 8/1994 | Nardella . |
| 5,431,649 | 7/1995 | Mulier et al. . |

(List continued on next page.)

Primary Examiner—Marvin M. Lateef
Assistant Examiner—Shawna J. Shaw

(57) ABSTRACT

To ablate target tissue a handle with proximal and distal ends connect to an interior passageway and along an axis. A semi rigid and helical effector at the distal end is along the axis and has a sharpened distal tip and a mount at its handle attachment. A source of radio frequency current supplies the effector and is insulated from the handle for delivery to bipolar and monopolar circuits. A return electrode connects between tissue and the source of radio frequency current. A sensor is carried on the handle positioned to measure target tissue ablation. A control couples the source of radio frequency current and the sensor for loop regulation of ablation. The effector is a wire bent into the helical shape with an insulating sleeve to prevent passage of radio frequency current near its mount. The sensor has a calculator to find impedance or temperature changes and the control examines for a rise. The effector is in an alternate a hollow tube bent into the helical shape and closed at its distal tip; the handle has a passage for fluid circulation. A return located on the effector insulating sleeve has a larger surface area than the distal tip. A bipolar delivery effector carries at least two electrodes supplied with current of opposite polarity between the electrodes. The effector is a framework with at least two supports for locating electrodes in spaced apart relationship about the distal tip. A plurality of electrodes are in an alternate coupled to the source of radio frequency current to receive opposite polarity from a multiplexer coupled electrically between the source of radio frequency current and the plurality of electrodes for selective delivery of radio frequency current of opposite polarity to at least two of the electrodes at the same time. An elongate shank extending from the mount to the helical shaped part of the effector for laparoscopic applications. A portal near the distal tip diverts the sensor to a position to measure target tissue. A light based system has a fiber optic for measurement of radiation of the target tissue with a meter. The control has a power modulator to maintain the impedance at approximately its low point. A method of ablating subsurface tissue includes inserting the distal tip into an entry point, rotating the effector about its axis to screw the helical shape into the tissue, and delivering controlled amounts of radio frequency current to the tissue.

42 Claims, 18 Drawing Sheets

U.S. PATENT DOCUMENTS

| | | |
|---|---|---|
| 5,488,958 | 2/1996 | Topel et al. . |
| 5,507,743 | 4/1996 | Edwards et al. . |
| 5,545,193 | 8/1996 | Fleischman et al. . |
| 5,549,644 | 8/1996 | Lundquist et al. . |
| 5,556,377 | 9/1996 | Rosen et al. . |
| 5,662,680 | 9/1997 | Desai . |
| 5,776,155 | 7/1998 | Beaupre et al. . |
| 5,797,956 | 8/1998 | Furnish et al. . |
| 5,800,378 | 9/1998 | Edwards et al. . |
| 5,810,806 * | 9/1998 | Ritchart et al. ................. 606/45 |
| 5,830,221 * | 11/1998 | Stein et al. ..................... 606/151 |
| 5,876,398 * | 3/1999 | Mulier et al. ..................... 606/41 |
| 5,919,187 * | 7/1999 | Guglielmi et al. . |
| 5,921,982 * | 7/1999 | Lesh et al. ........................ 606/41 |
| 5,941,893 * | 8/1999 | Saadat ............................. 606/180 |
| 5,976,121 * | 11/1999 | Matern et al. ....................... 606/1 |
| 6,017,358 * | 1/2000 | Yoon et al. ...................... 606/205 |
| 6,024,741 * | 2/2000 | Williamson, IV et al. ....... 606/40 |
| 6,090,105 * | 7/2000 | Zepeda et al. . |

\* cited by examiner

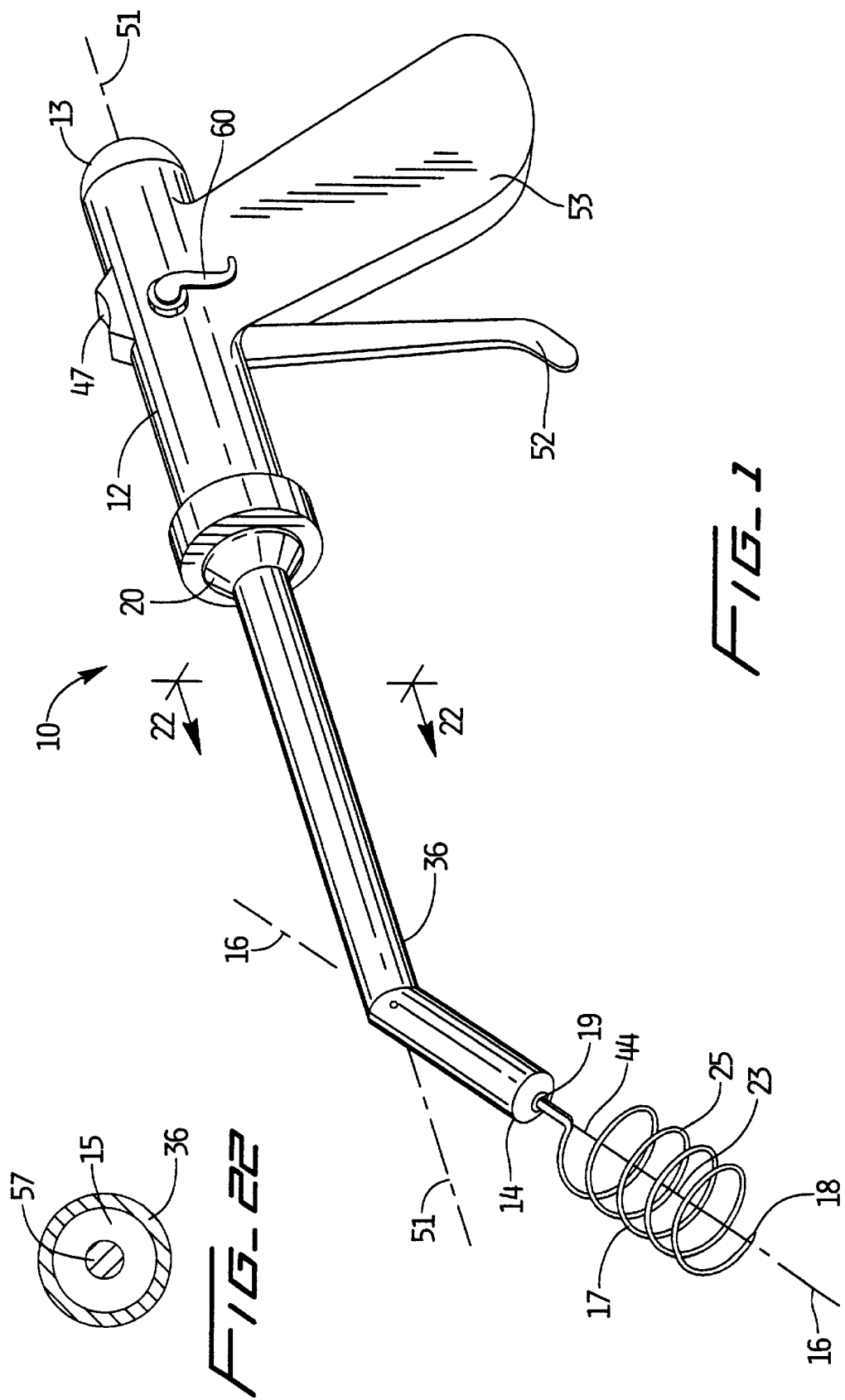

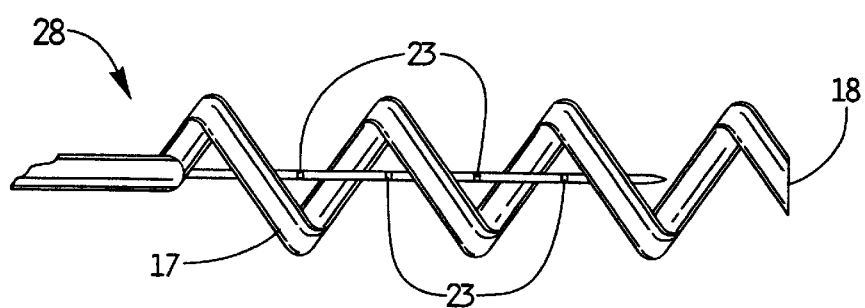
FIG_2
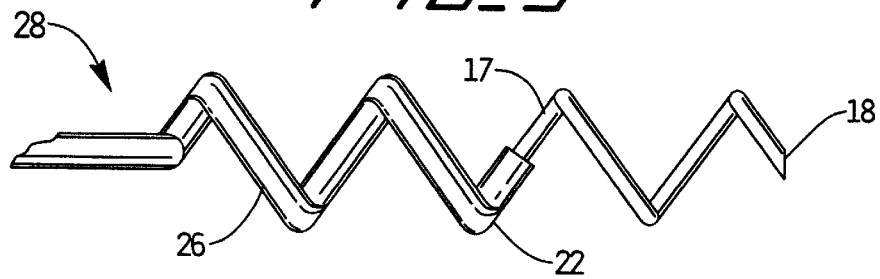
FIG_3
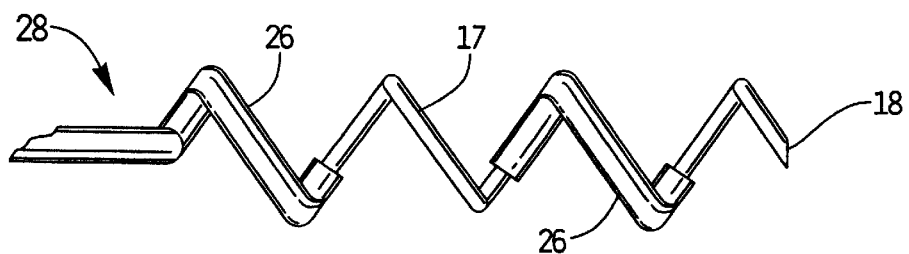
FIG_4
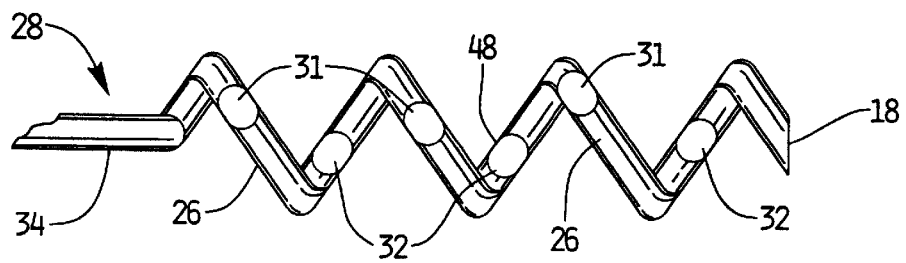
FIG_5

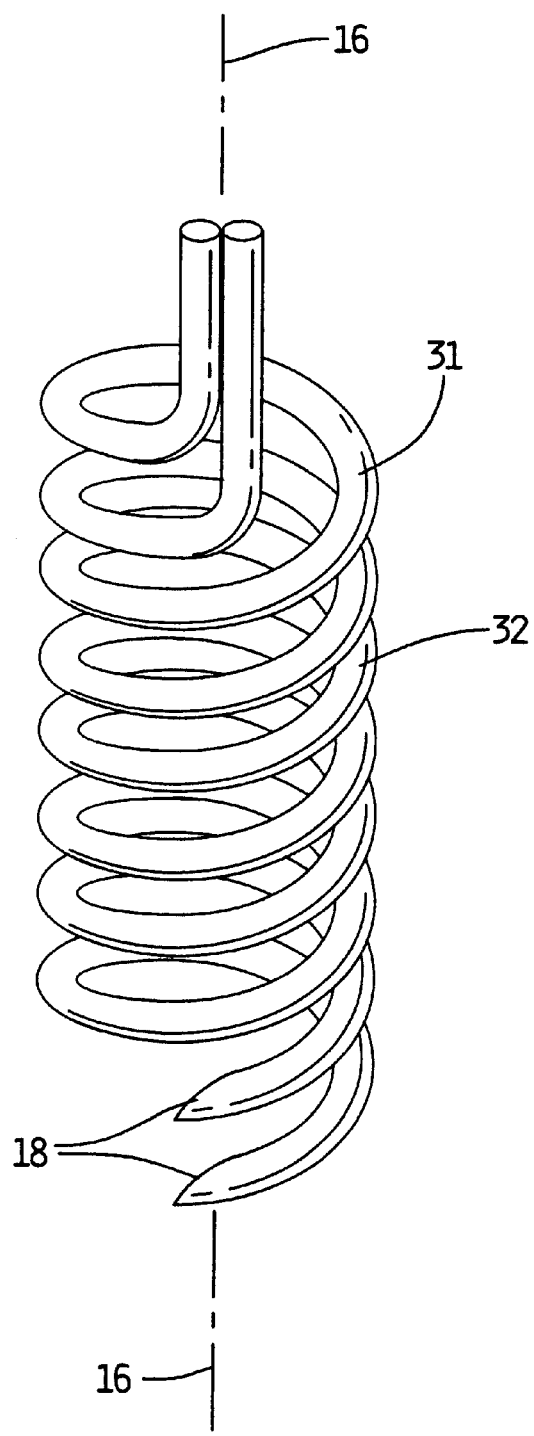
FIG_6

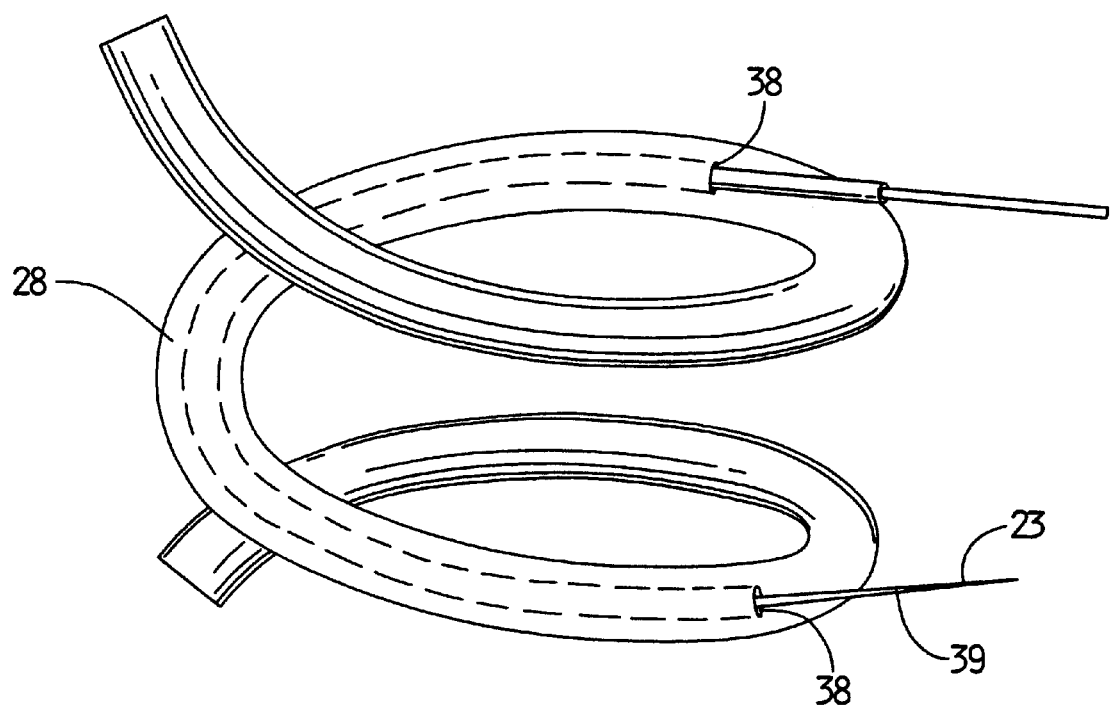
FIG_8

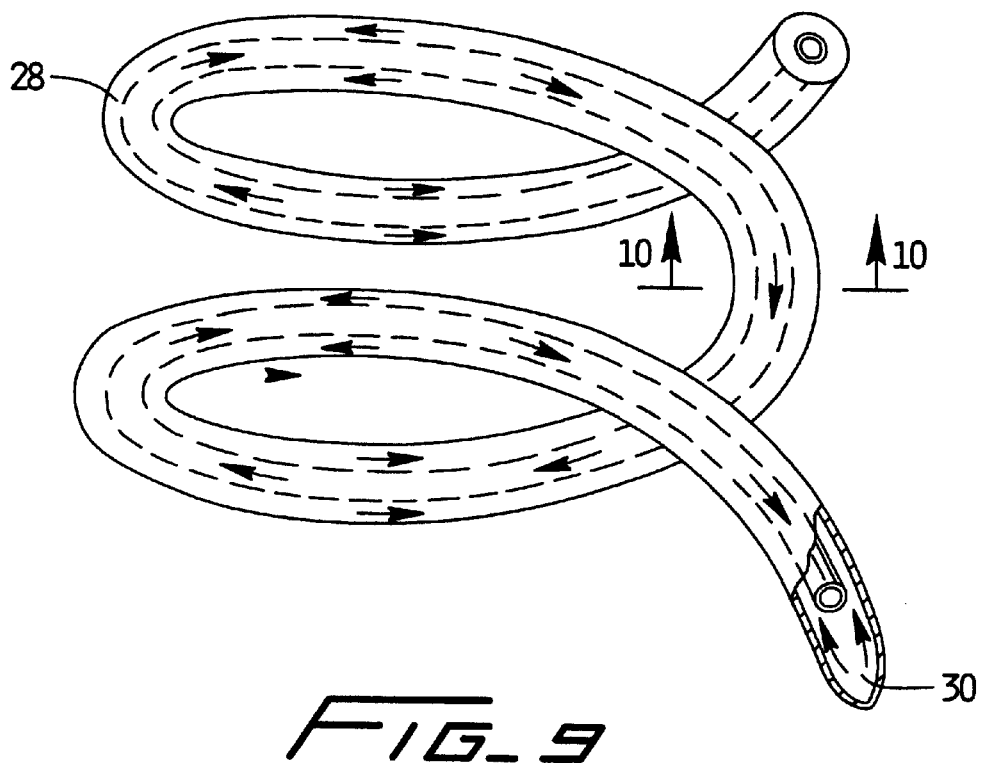
FIG_9
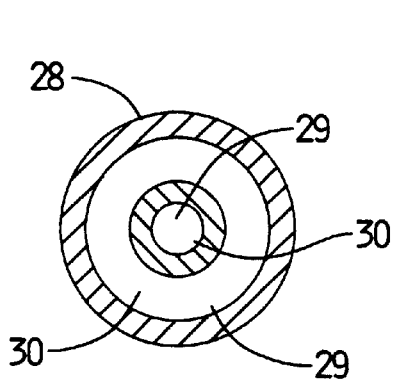
FIG_10
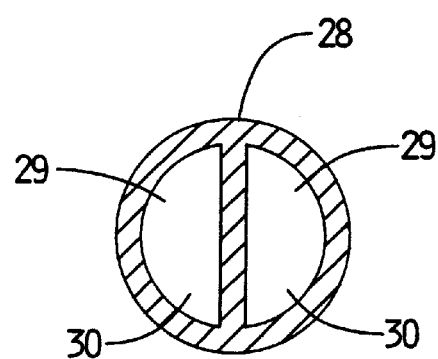
FIG_11

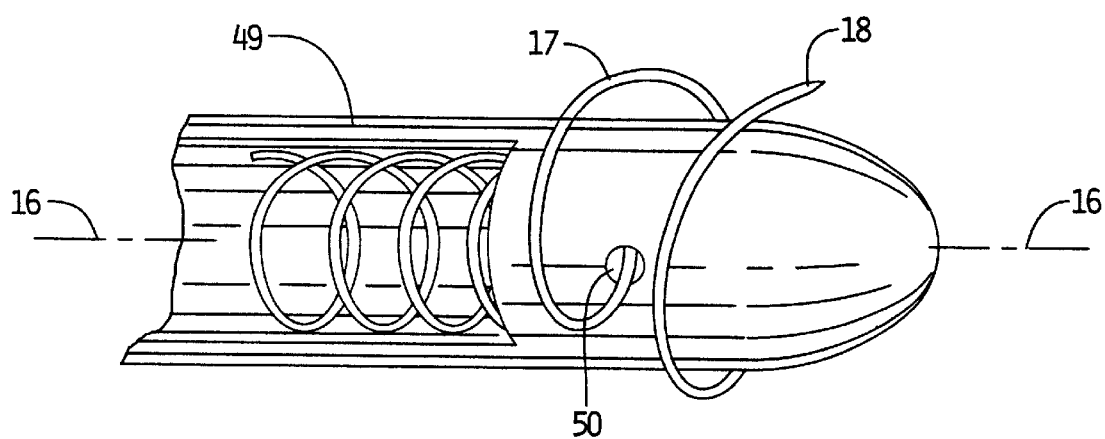
FIG_12

FIG_13
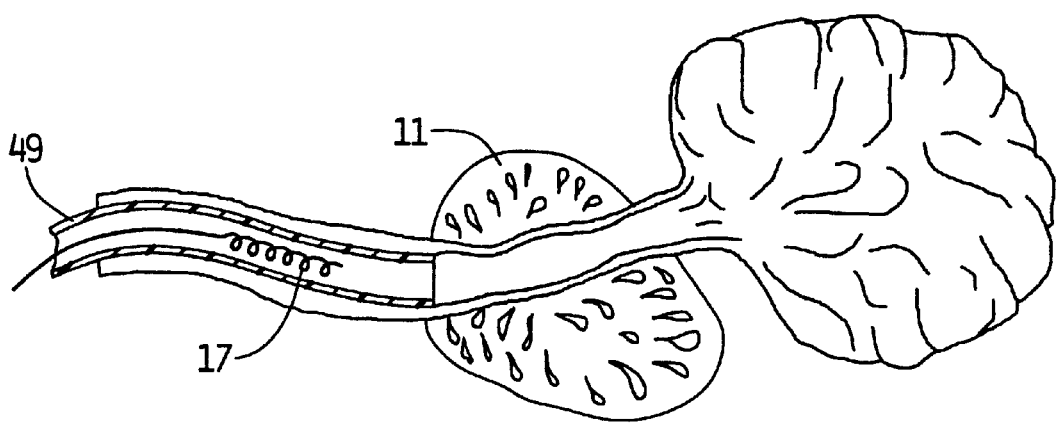
FIG_14
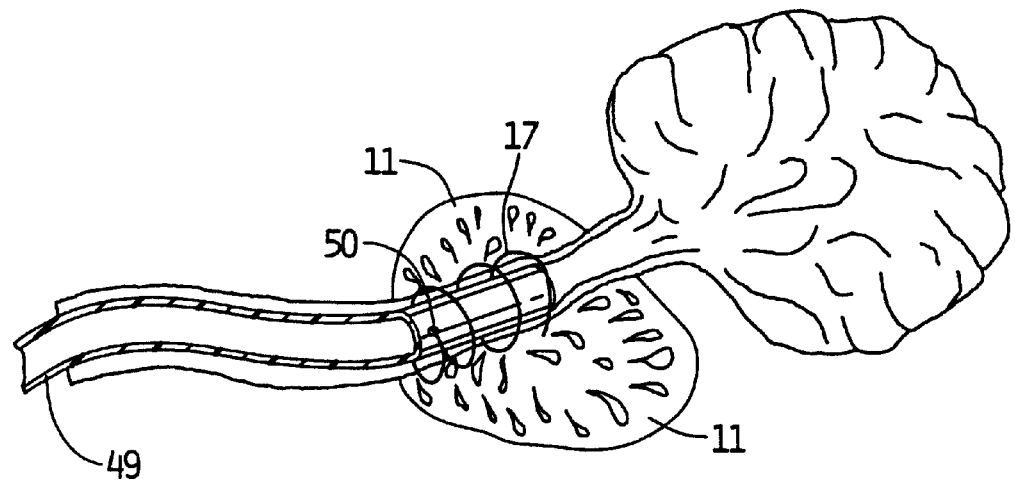

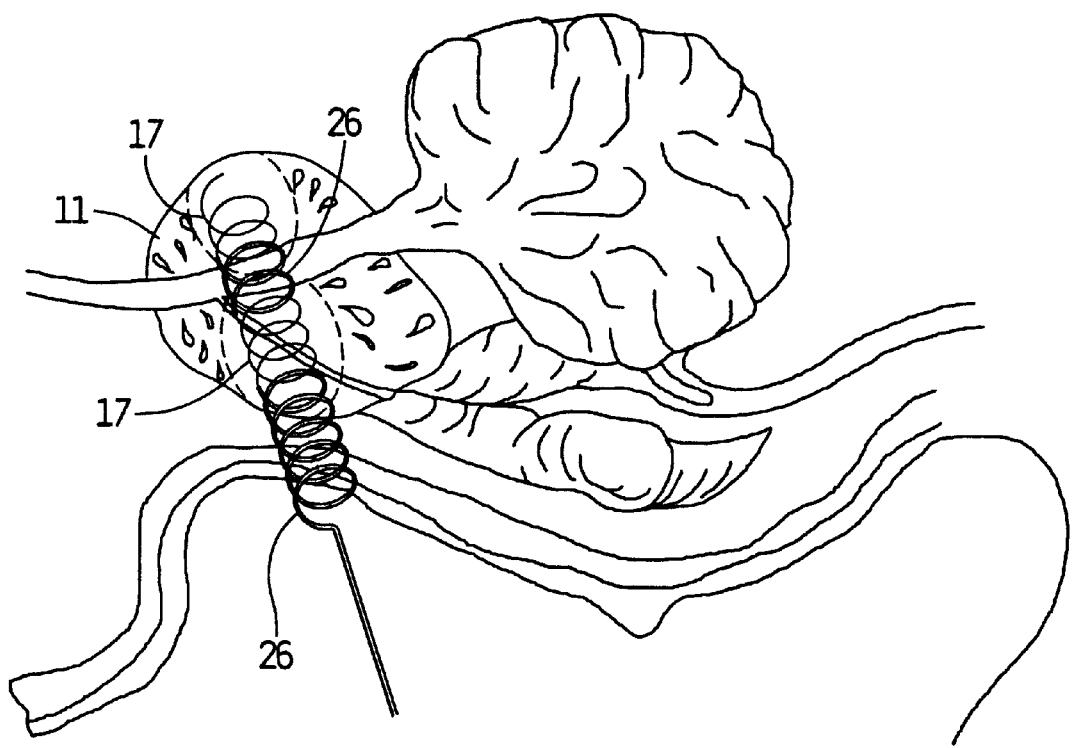
FIG_15

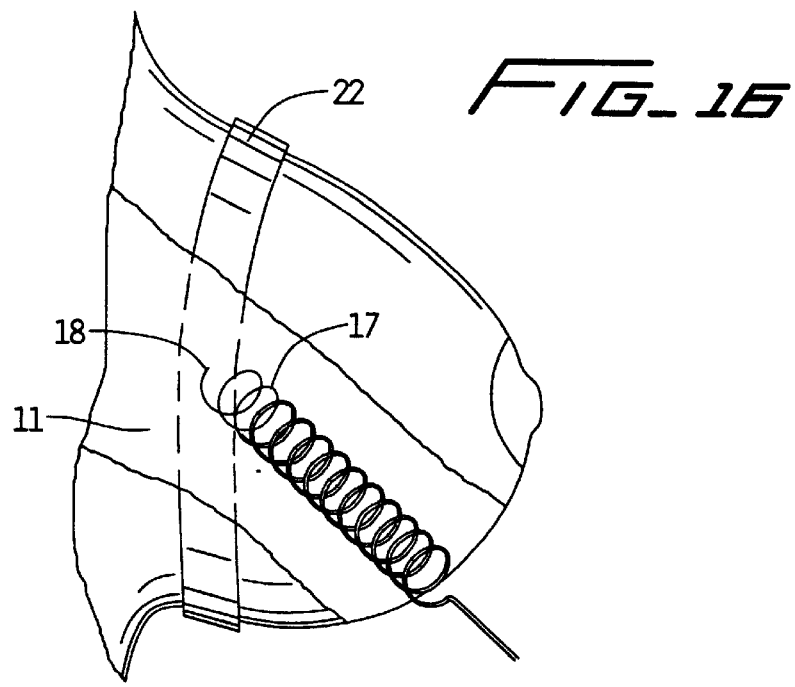
FIG_16
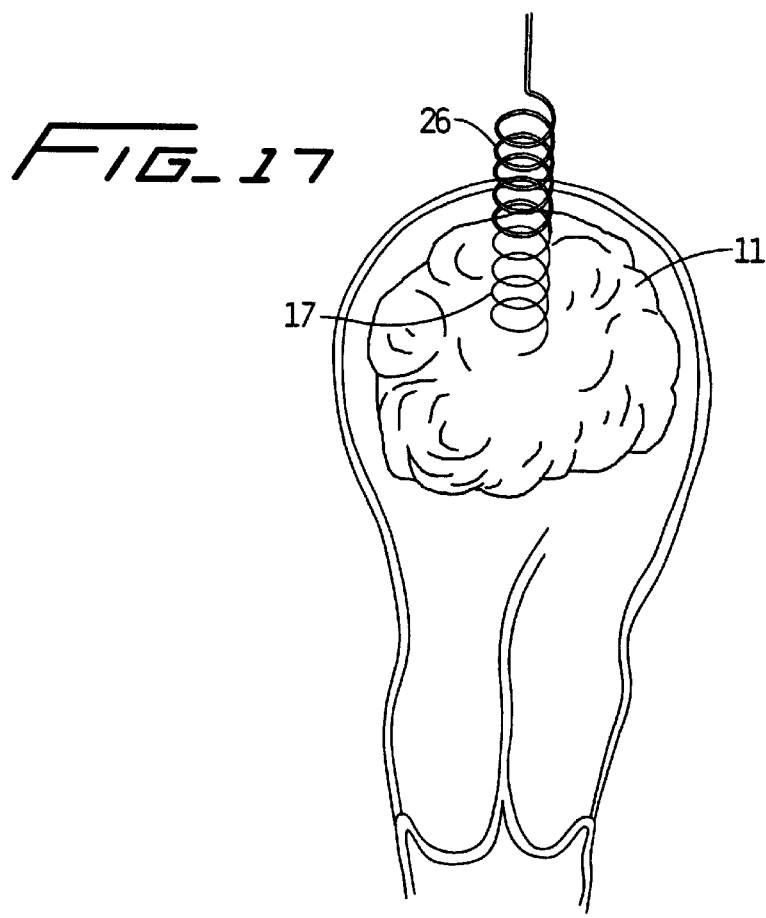
FIG_17

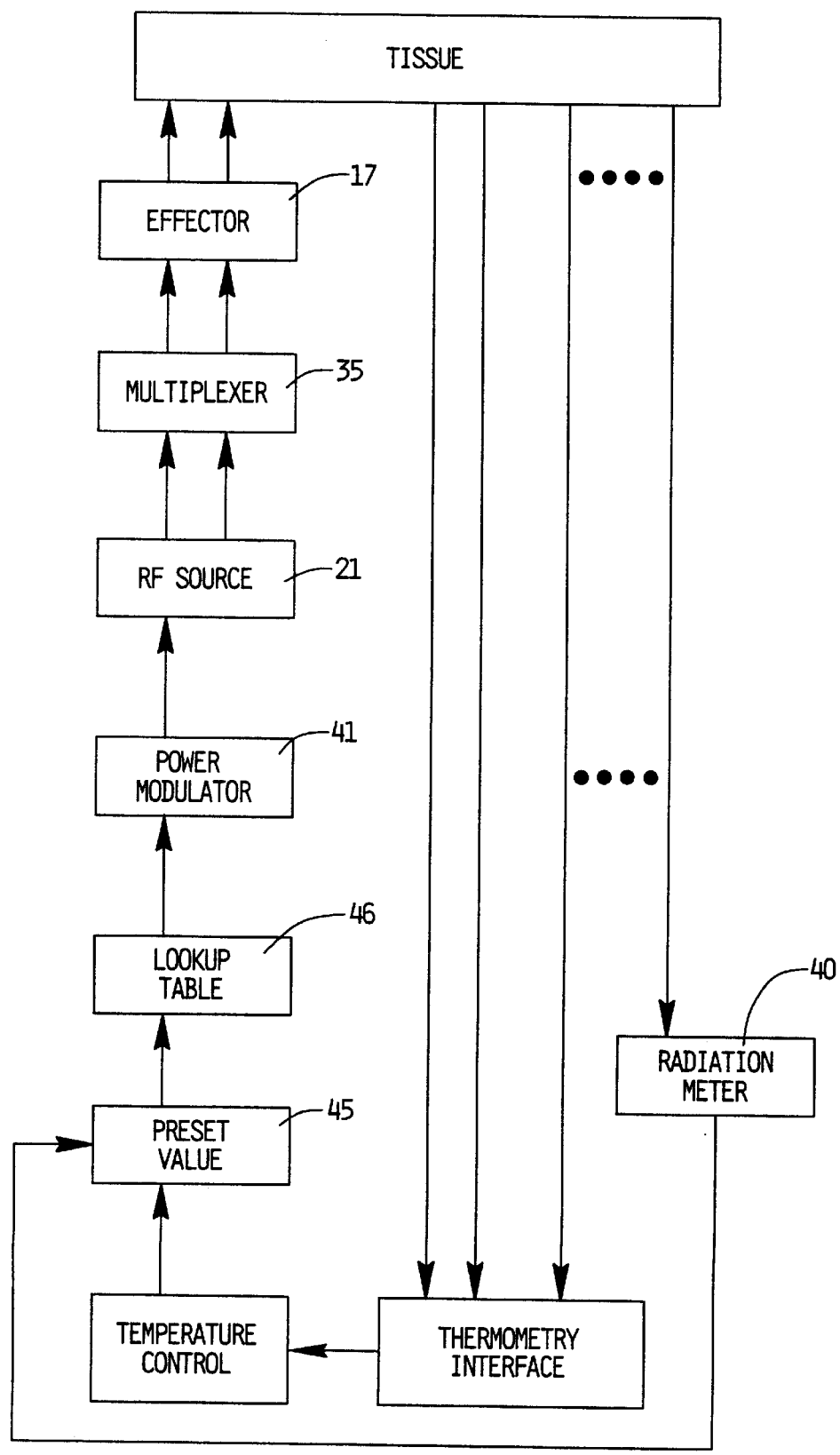
FIG_18

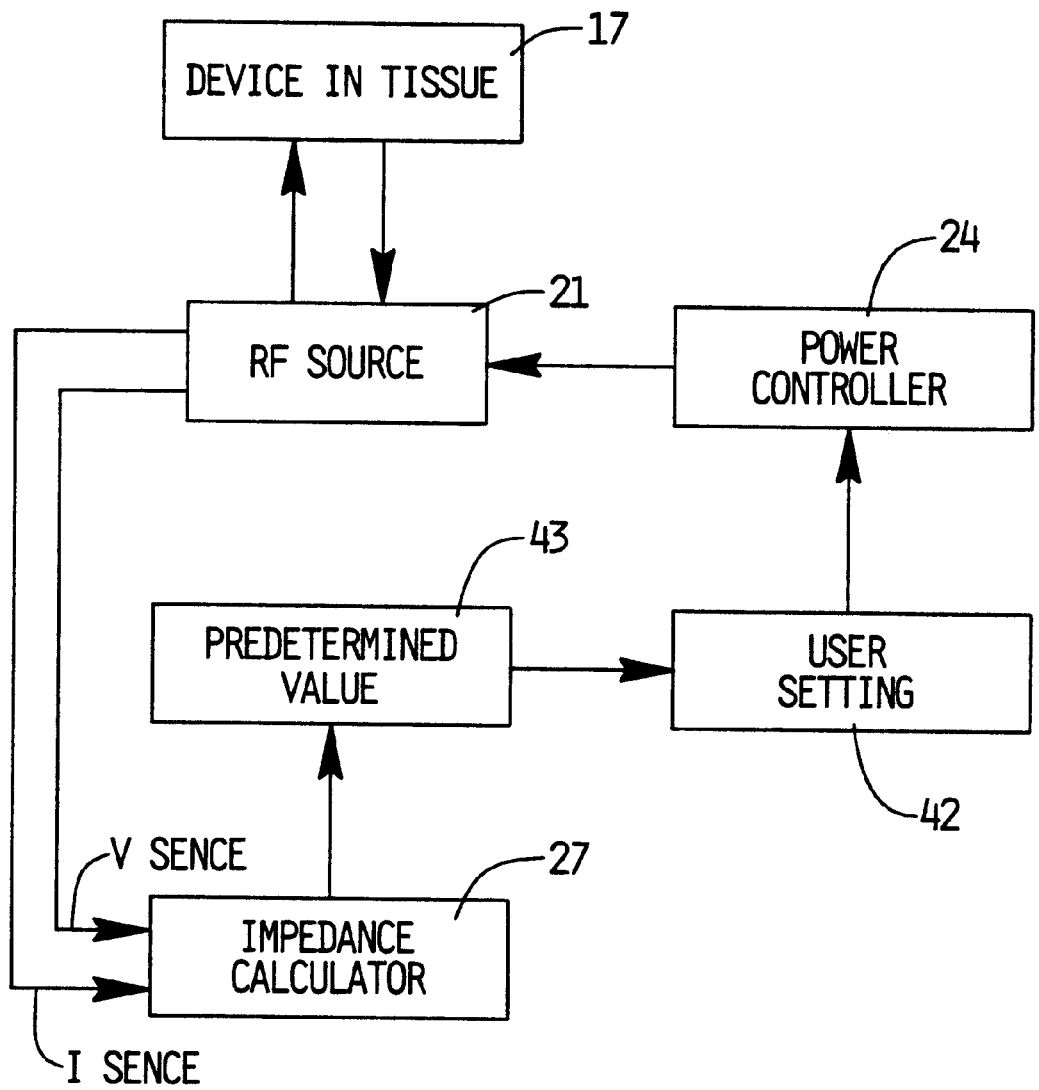
FIG_19

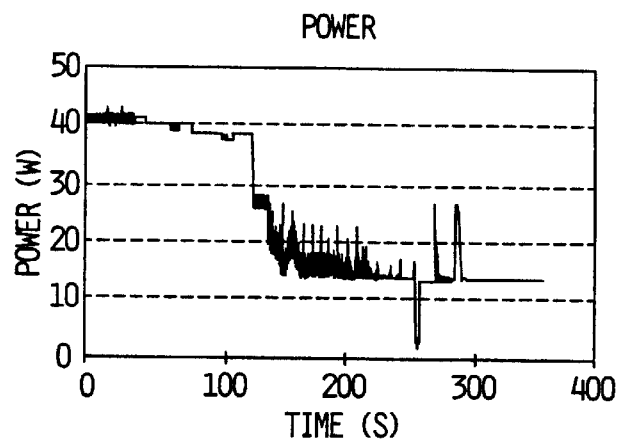
FIG_20A
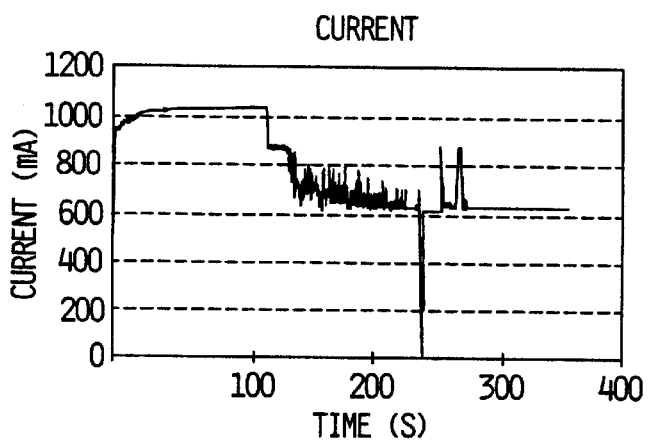
FIG_20B
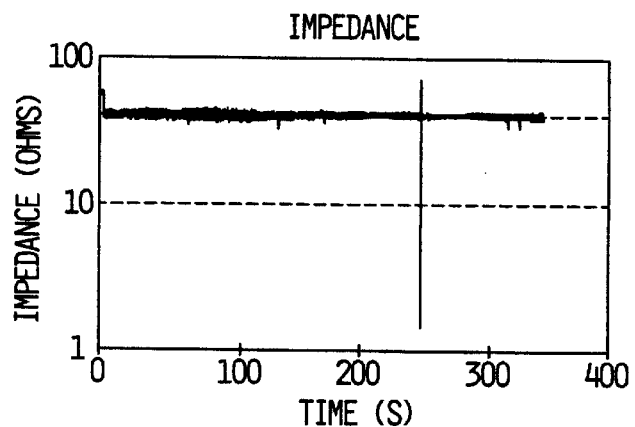
FIG_20C

FIG_20D
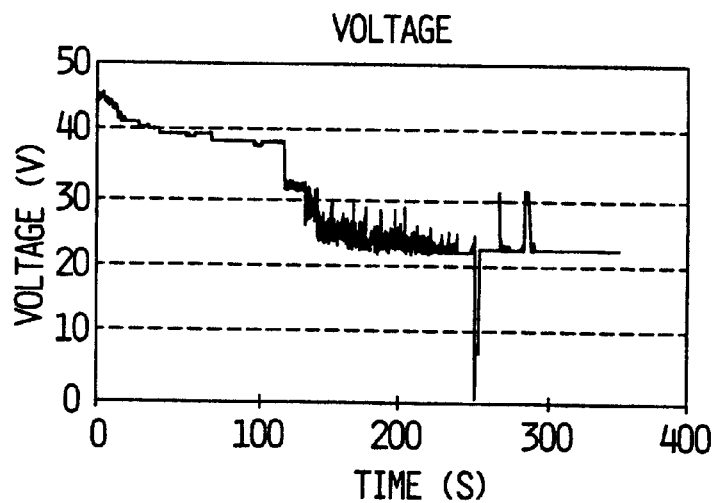
FIG_20E
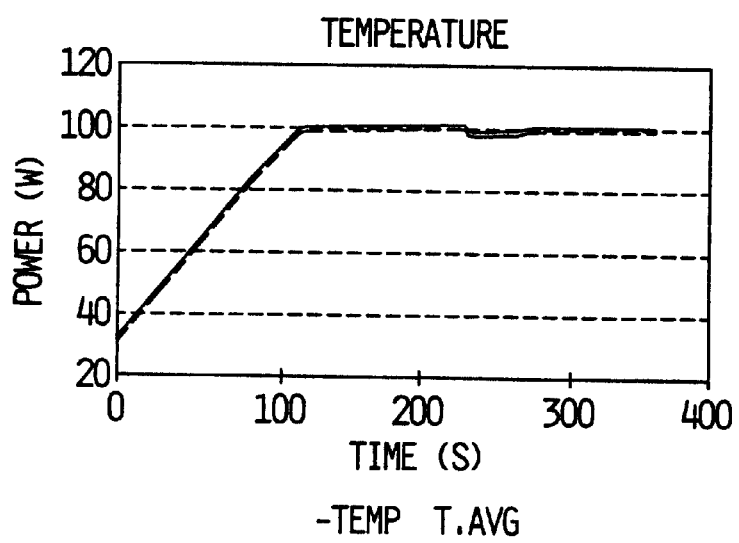
-TEMP T.AVG

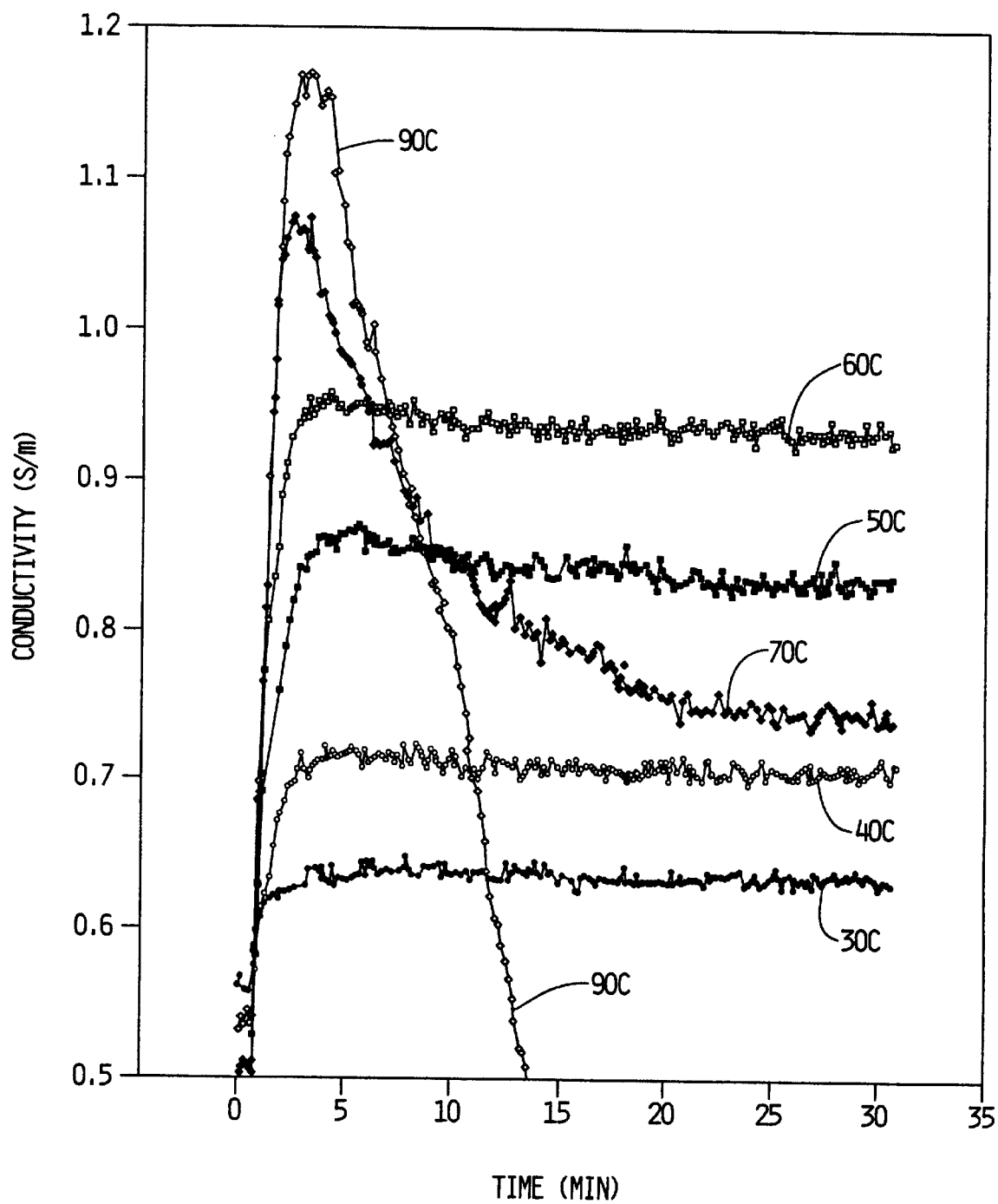
FIG_21

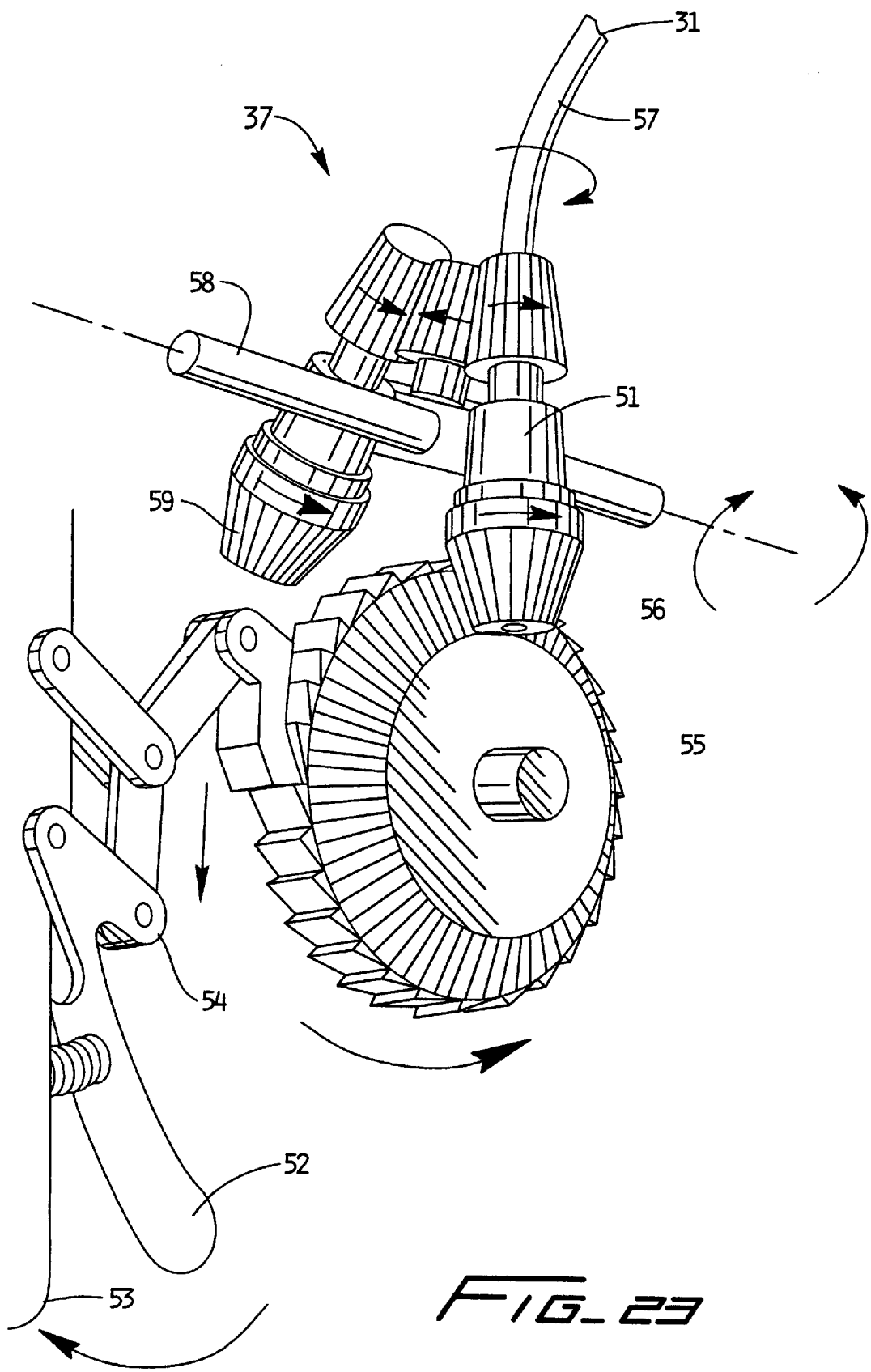
FIG_23

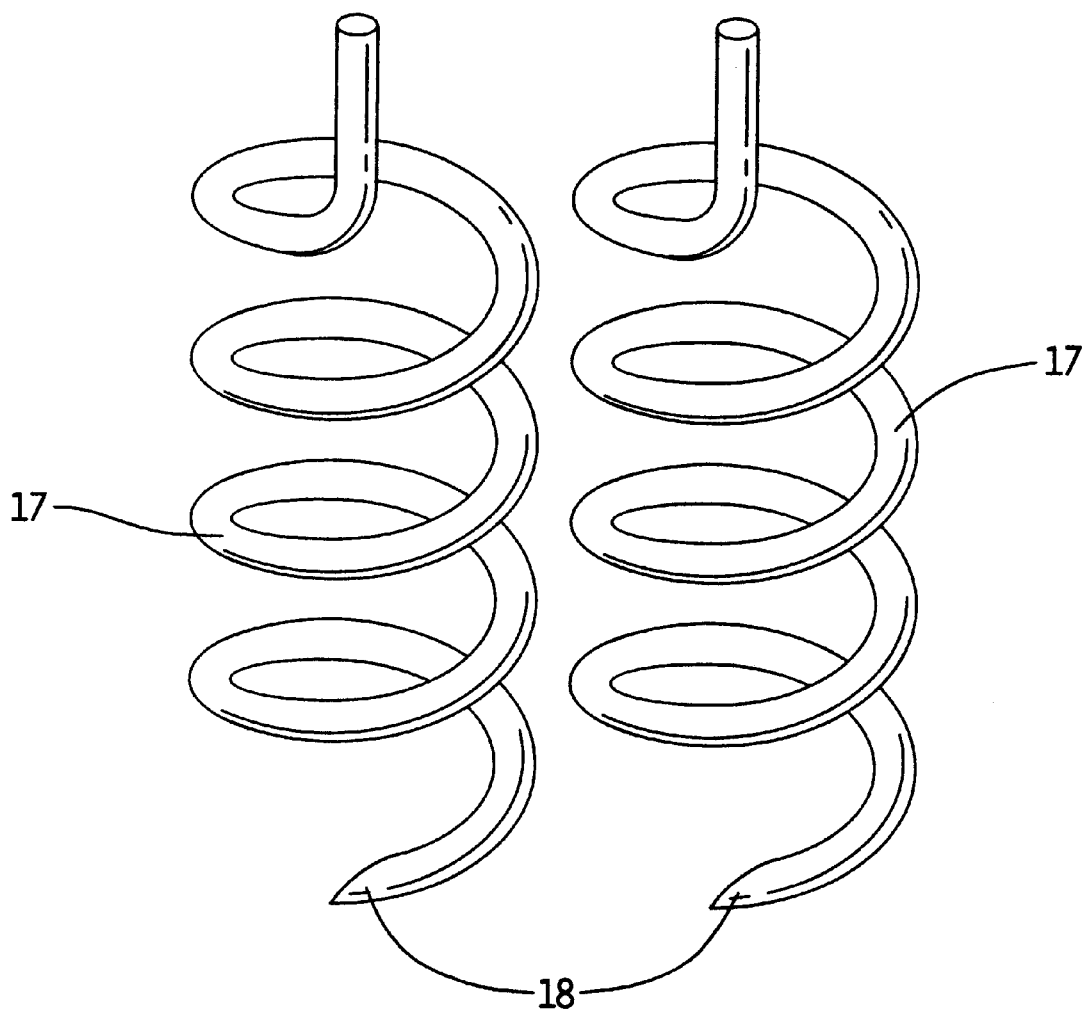
FIG_24

APPARATUS AND METHOD FOR RF LESIONING

1. Field of the Invention

This relates to an apparatus and method for ablating target tissue. More particularly, a temperature controlled monopolar or bipolar device placed in target tissue to create thermal lesions in the breast or in uterine myomas or fibroids or the prostate.

2. Background of the Disclosure

U.S. Pat. No. 4,010,758 discloses an annular, flat electrode that serves as ground with a helix that bores into tissue as the active electrode. The electrode can be insulated in order to separate it from ground. The device is made to screw into the heart and it is used for cardiac pacemaking by supplying a small electrical pulse, not for lesioning as in the present invention.

U.S. Pat. No. 4,637,392 discloses a doubly wound helix that is used for coagulation of blood in a wound. It is attached to an electric motor for rotation of 150–200 RPMs for cleaning ducts or pockets of tissue. A stationary scraper is also disclosed to clean the electrode as it rotates.

U.S. Pat. No. 4,945,912 discloses a helical antenna operational in the microwave frequency range. The helix is not in direct contact with tissue and is covered by a Teflon polymer sheath. It is designed for cardiac ablation and offers intracardiac monitoring of cardiac electrical activity.

U.S. Pat. No. 5,047,026 discloses a device for tunneling into or through tissue or a blood vessel. It is flexible to fit through an endoscope and operates over-the-wire. The guide wire is active and the helix is ground. The helix is tightly wound around a plastic core, requiring many turns to maximize surface area and to minimize current density.

U.S. Pat. No. 5,047,027 discloses a device for tumor resection that is composed of a multi-winding helix on a plastic holder and a loop. The helix is ground the loop is active for cutting and resecting tissue.

U.S. Pat. No. 5,100,423 discloses an over the wire device made to clean clogged blood vessels. It is composed of helical wires that can be activated with RF energy to cut through plaque or vibrate by using ultrasound to increase the effect. It is shaped like a wire basket.

U.S. Pat. No. 5,507,743 is a combination of straight electrodes and helical electrodes on the outside of the straight electrode. Energy is activated between electrodes using an RF source. It has variable pitch deployment that allows for a compact size when undeployed. There are thermal sensors on the outside of the needles for feedback control. No frequencies or temperatures are measured. There are no thermal sensors in tissue in the target treatment area. The needles are hollow and have exit ports for drug infusion.

U.S. Pat. No. 5,431,649 discloses a catheter based helix that screws into tissue for ablation. A conductive solution is applied through side ports in the needle. The helix has variable insulation localization. There are sensors in the needle for temperature feedback control, but no sensors in tissue.

U.S. Pat. No. 4,800,395 discloses a helix as part of an antenna system operational in air. It couples to a monopole antenna for communications. U.S. Pat. No. 5,226,890 discloses a tissue gripping device with helical threads on the outside of a trocar to bore into tissue. U.S. Pat. No. 5,488,958 discloses a surgical cutting instrument where a helix bores into tissue for the purpose of providing mechanical advantage for a cutting shaft to then follow the helix and core out the tissue. U.S. Pat. No. 5,334,193 discloses a fluid cooled ablation catheter that operates by monopolar RF or by bipolar by having two helices wound around a catheter shaft. The device ablates tissue by passing over the tissue as in a lumen, rather than boring into tissue as in the present invention.

U.S. Pat. No. 5,545,193 discloses a device that is composed of a wire cage that could be helical wound for treating hollow organs and does not have temperature feedback, nor does it bore into tissue.

U.S. Pat. No. 5,662,680 discloses an irrigation and suction device that carries various needle arrangements endoscopically for tissue ablation. There is no helix configuration for boring into tissue.

As seen in the prior patents, there are many uses for helical shapes including tissue removal or tissue ablation. None of the disclosures combines all of the factors of the present invention with a helix that penetrates into tissue, temperature feedback control in the tissue instead of on the helix shaft, and the potential for closed ended fluid circulation for cooling.

Many attempts to ablate tissue percutaneously or through body orifices have been tried. The target tissue could be any contained malignancy or metastasis in the breast, liver, pelvis, or other site. The target tissue could also be a benign disease that is causing patient discomfort, bleeding or obstruction, such as prostate and myomas. The tissue could also be endometrium patches causing endometriosis or a disc herniation in the spine. The purpose of the lesioning is to ablate the tissue and defunctionalize it with subsequent fibrosis and absorption. RF delivery systems have been simply comprised of 1 needle in monopolar mode or 2 or more needles in bipolar mode. Due to the lack of significant penetration because of localized RF current, the depth of penetration of RF is limited without some sort of enhancement. This enhancement could be cooling, changing frequency or changing the electrode configuration geometry. The puncture or entry sites are of limited diameter, thus the probes must somehow have an efficient geometric shape to affect large areas for ablation without undue trauma in getting the device in place.

SUMMARY OF THE INVENTION

The current device is either a rigid or deployable design of either monopolar or bipolar design with a single entry site, not an array of needles. The rigid design is a helical shaped effector that is screwed into the tissue target. The entry consists only a small puncture site. The helical shaped effector is either a single conductor for monopolar activation or bipolar with alternating segments or alternating coils connected to a bipolar RF supply. The shaft of the helical shaped effector may be hollow to allow coolant circulation. This will enhance the heating penetration by overcoming the intense thermal gradients in the near field. Other embodiments are deployable devices that enter the target tissue in a compressed or folded state and then are expanded into the target tissue to create a devices that spreads out into the target tissue. These can also be monopolar designs or have electrically separate segments that are connected in a bipolar configuration. Cooling can enhance many of these designs and the coolant can be either air or fluid. The water cooled systems can be either pump fed or gravity fed with a pressurized IV bag. There may be a thermocouple inside of the device to provide temperature feedback and a means to control.

The current method is to place the device into the target tissue either by rotating through a small skin entry point or the surface of the target tissue. Power and/or current can be carefully controlled either by sensing temperature at the needle site or central to the helical shaped effector or at the edge of the lesion. Cooling can be added to enhance the size of the treated region. The lesion is then created over 2–12 minutes, preferably about 4–6 minutes in a gradual fashion to prevent target tissue adherence of the electrode and coring of the target tissue by removing a central block as the electrode is removed after treatment. Temperatures are limited in the central portion of the ablation volume to 95–105° C. to avoid the effects of steam formation and target tissue adherence to the device. The return pad may encompass the target organ or be placed elsewhere on the body. For precise control of the lesion, thermometry probes may be placed as follows: on or in the helical shaped effector at various locations, in the target tissue in the center of the helical shaped effector, or in the target tissue at the edge of the intended lesion.

For insertion into target tissue, especially rubber-like target tissue as found in myomas, the helical shaped effector may be on a handle that turns to drive the helical shaped effector deep into target tissue by a ratchet activation that corresponds a certain number of turns beneath the surface. A typical helical shaped effector size is 17 gage shaft size, 15 mm diameter, 10 mm pitch, and 15 cm length. It could of course be a different pitch, diameter and shaft diameter depending on the application and target lesion volume.

The helical shaped effector aids in the delivery of the device in target tissue, since once a small puncture is made, the needle continues to bore into target tissue, thus facilitating accurate trajectory of the device as well as accurate depth localization. Thermal conduction fills in the space between the helical windings, both internal to the helical shaped effector and outside thereof between windings. With relatively low power per surface area ($W/mm^2$) delivered, the helical shaped effector does not overheat the target tissue in direct contact with the shaft of the helical shaped effector, thus avoiding raising impedance and the load seen by the generator. Temperature feedback is used to control the rise of temperature in the target tissue, as well as the steady-state target temperature control in the target tissue.

The helical shaped effector heats both radially outward from its axis and beyond the tip and above any upper insulated boundary. With control of temperature, the amount of steam formation, charring, or smoke formation is minimized, especially at the location of the helical shaped effector-target tissue interface. The lesion will of course grow in size with extended time periods of power application, but parameters were chosen to optimize the lesion size in 6–12 minutes.

The parameters of power delivery are target tissue specific, owing to the different electrical and thermal properties of various target tissue types. For example, the parameters used to heat muscle or liver to maximize lesion size would not be the same as heating fat which has a higher electrical resistivity, but lower thermal conductivity.

If done optimally, that is, avoiding target tissue charring and steam formation, the helical shaped effector only leaves small holes in the target tissue as seen when the target tissue is cut along the long axis of the helical shaped effector. Other factors in the construction of the helical shaped effector for optimal lesion creation are the outside diameter of the windings, the shaft or wall thickness, and the pitch (spacing between the windings). Dimensions that work well in several target tissue types are 16 mm diameter, 1.6 5mm shaft thickness, and 10 mm pitch. If the helical shaped effector outside diameter is too large the inner volume will not heat well due to the slow thermal conduction inward. Also, if the pitch is too large, excessive temperature gradients will exist and heating will be non-uniform.

By insulating or plating only certain portions of the helical shaped effector such that some regions are insulated from current flow and some are conductive to current flow, the active and inactive regions of the helical shaped effector can be controlled. In this manner, a deep lesion can be targeted without any heating near the surface of the skin.

For deeper penetration into target tissue without changing the size of the applicator, cooling can be used. Cooling lowers the temperature of the helical shaped effector and the target tissue in immediate contact with the helical shaped effector. This allows greater power delivery without overheating the zone of target tissue in direct contact with the helical shaped effector.

The helical shaped effector can be delivered in a number of methods. A ratchet on the handle moves the helical shaped effector a fraction of a turn with each squeeze of the handle, press of a button or knob, or linear movement of a slider. The thermal probes can be inside of needles or catheters which are guided by a template which also guides the helical shaped effector to assure correct positioning.

BRIEF DESCRIPTION OF THE DRAWINGS

FIG. 1 is a perspective view of an electrosurgical apparatus adapted for ablating target tissue within a body with a helical shaped effector as on a laparoscopic instrument.

FIG. 2 is an enlarged side view of the distal tip of the effector wherein a temperature probe is along an axis thereof.

FIG. 3 is an enlarged side view of the distal tip of the effector wherein a the proximate end of the effector is insulated to prevent passage of radio frequency current.

FIG. 4 is an enlarged side view of the distal tip of the effector wherein different areas are active for delivery of radio frequency current.

FIG. 5 is an enlarged side view of the distal tip of the effector wherein electrodes of different polarity are shown for delivery of radio frequency current.

FIG. 6 is an enlarged side view of the distal tip of the effector wherein one helix is shown inside of another helix along the same axis for delivery in a bipolar circuit therebetween of radio frequency current or delivery of monopolar radio frequency current to a return in a monopolar circuit.

FIG. 8 is an enlarged side view of the distal tip of the effector wherein the probe is shown threaded through only a portion of the helical shaped effector.

FIG. 9 is an enlarged side view of the distal tip of the effector wherein a hollow effector has two coolant passages for permitting flow of coolant therethrough.

FIG. 10 is a view in cross section taken along line 10—10 in FIG. 9 of the relationship of the coolant passages shown therein.

FIG. 11 is a view in cross section similar to FIG. 10 of the relationship of the coolant passages but shown as a double d tube.

FIG. 12 is an enlarged side view of the distal tip of the effector wherein the helical shaped effector passes through a side portal and expands into and through the target tissue as it is screwed thereinto.

FIG. 13 is an enlarged side view of the distal tip of the effector wherein the prostate is to be treated with a distal tip as shown in FIG. 12.

FIG. 14 is an enlarged side view of the distal tip of the effector wherein the helical shaped effector of FIG. 13 is shown deployed and expanded into the lobes of the prostate.

FIG. 15 is an enlarged side view of the distal tip of the effector wherein a helical shaped effector is transrectally delivered and the distal tip includes area insulated to prevent delivery of radio frequency current to non target tissue such as the urethra and the rectum.

FIG. 16 is an enlarged side view of the distal tip of the effector wherein the distal tip is inserted into the breast and the return as wrapped about the outside thereof for a monopolar radial delivery of radio frequency current to the target tissue disposed about the distal tip.

FIG. 17 is an enlarged side view of the distal tip of the effector wherein a distal tip is shown inserted in through the fundus to penetrate a myoma in the uterus for the delivery of radio frequency current to that target tissue.

FIG. 18 is a schematic block diagram of a circuit used to control, regulate and loop the delivered radio frequency current.

FIG. 19 is a schematic block diagram of a circuit for the impedance calculator used to find the measured impedance from voltage and current values.

FIG. 20 are plots of the measured values of temperature, power, voltage current and impedance during a treatment with a helical shaped distal tip of target tissue.

FIG. 21 are graphs of conductivity over time at different temperatures showing the differences in the target tissue treatment as a family of curves.

FIG. 22 is a view in cross section through a port in FIG. 1 as seen along lines 22—22 in FIG. 1.

FIG. 23 is a perspective view of a twisting mechanism.

FIG. 24 is a view of two helical shaped effectors extending to their distal tips for use as electrodes and shown substantially parallel to one another but they need not be.

DETAILED DESCRIPTION OF THE INVENTION

Figure 7:
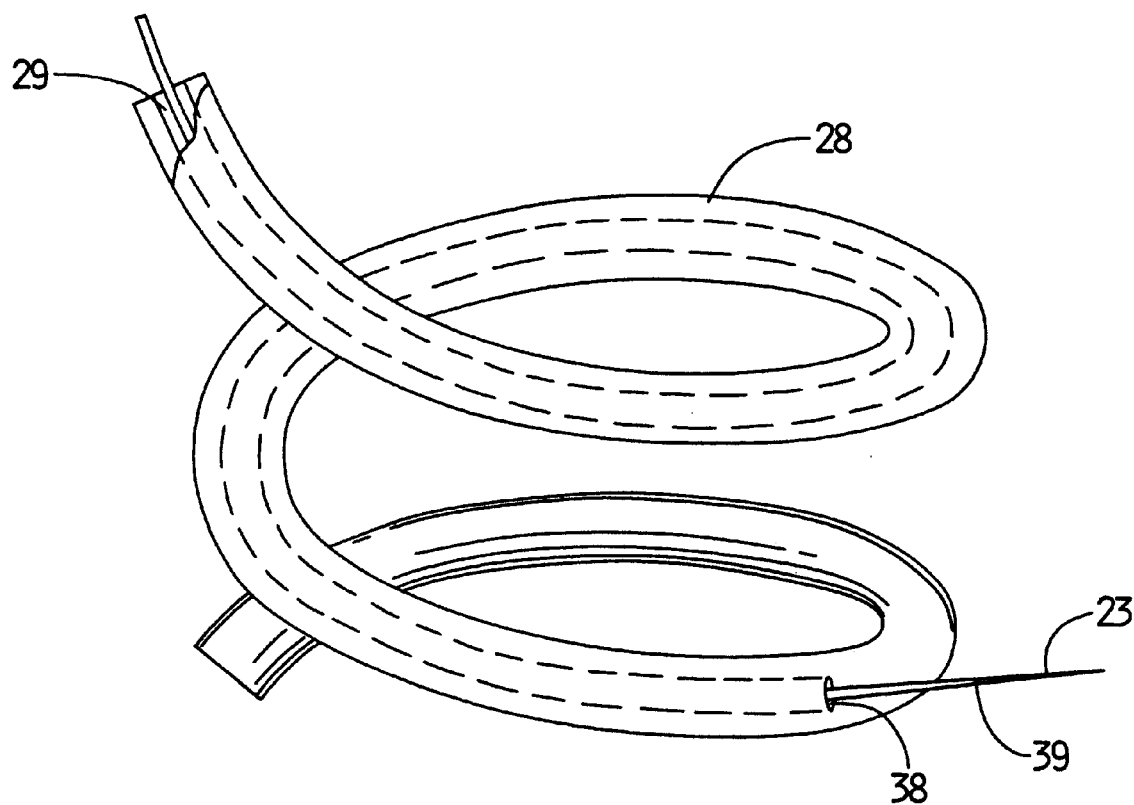
FIG. 7 is an enlarged side view of the distal tip of the effector wherein a helical shaped effector has a hollow therein for a probe to pass before exiting to be placed in the target tissue.

An electrosurgical apparatus 10 in FIG. 1 adapted for ablating target tissue 11 within a body has a handle 12 having a proximal end 13, a distal end 14 along an axis 16 and an interior passageway 15 along an axis 51 through the handle 12. An effector 17 carried at the distal end 14 is semi rigid and of primarily helical shape extending along the axis 16 of the handle 12. The effector 17 has a sharpened distal tip 18 at one end and a mount 19 at its opposite handle attachment 20. A source of radio frequency current 21 couples to the effector 17 and is insulated from the handle 12. A Force FX™ electrosurgical generator preferably provides controlled radio frequency current delivery bipolar and monopolar circuits and is made and sold by Valleylab Inc of Boulder, Colo.

If either a monopolar or, a bipolar then a return electrode 22 therein in contact with tissue 11 is located between the source of radio frequency current 21 and the effector 17. A sensor 23 is carried on the handle 12 in position to measure within the target tissue 11 the extent of ablation about the effector 17 due to the passage of radio frequency current through the target tissue 11. A control 24 coupled between the source of radio frequency current 21 and the sensor 23 to effect a loop regulation of the delivery of the radio frequency current defines the extent of ablation. The loop regulation could include proportional control or other controls as found in fuzzy logic and neural networks in order for the temperature to follow any preset target to ramp up to the selected target with minimal overshoot of the goal as seen in FIG. 20. The control 24 need not be within the source of radio frequency current 21, but could be integral therewith as in the Force FX™ generator.

The effector 17 is in one form a wire 25 bent into the helical shape with an insulating sleeve 26 (not shown in FIG. 1 but illustrated in FIGS. 2 through 5) surrounds the wire 25 to prevent the passage of radio frequency current from the effector 17 near the mount 19 to the handle 12 so that the ablation is in the target tissue 11 positioned about the distal tip 18, as shown in FIGS. 3 and 17. Another embodiment is shown in FIG. 5 with the possibility of alternate polarity of electrodes 31 and 32 and separated by insulating sleeve 26. Thus that embodiment could be used in either a monopolar fashion or bipolar fashion. The sensor 23 includes a calculator 27 in FIG. 19 to find impedance changes during the delivery of radio frequency current to the target tissue 11 as the control 24 examines the impedance changes for a rise in the calculated impedance. The effector 17 is in an alternate form a hollow tube 28 bent into the helical shape and the handle 12 includes a passage 29 for fluid 30 circulation within the hollow tube 28. The hollow tube 28 is closed at its distal tip 18.

In FIG. 3 the insulating sleeve 26 is shown extending part way over effector 17 the amount of extension over hallow tube 28 or wire 25 can vary. In another embodiment, the return electrode 22 is located on the effector 17 insulating sleeve 26 in FIG. 3. The return electrode 22 has a larger surface area than the distal tip 18 for delivery of radio frequency current. That is to say that the return electrode carries lower watt density per unit area than the distal tip 18 so that the treatment by ablation is primarily about the distal tip 18. The effector 17 when used for bipolar delivery carries at least two electrodes 31 and 32 supplied by the source of radio frequency current 21 see FIG. 6. At least two electrodes 31 and 32 are supplied with current of opposite polarity as a bipolar circuit between the electrodes 31 and 32, as seen in FIG. 5. The electrodes 31 and 32 are carried on the effector 17 helical shape and wherein the effector 17 is a framework with at least two supports 34 for the at least two electrodes 31 and 32 located in spaced apart relationship about the distal tip 18.

A plurality of electrodes 31 and 32 in FIG. 5 are in another alternate coupled to the source of radio frequency current 21 to receive opposite polarity from a multiplexer 35 in FIG. 18 coupled electrically between the source of radio frequency current 21 and the plurality of electrodes 31 and 32 for selective delivery of radio frequency current to at least two of the electrodes 31 and 32 of opposite polarity at the same time. The effector 17 between its mount 19 and distal tip 18 has an elongate shank 36 extending from the mount 19 to the helical shaped part of the effector 17, as seen in FIG. 1. The laparoscopic applications the shank 36 can be rather long. The handle 12 includes a twisting mechanism 37 in FIG. 23 connected to the mount 19 to rotate the effector 17 about its axis 16 during insertion of the distal tip 18 into the target tissue 11 of the body. Mechanism 37 has an actuator 52 on handle 53 at the surgeon end. The actuator 52 connects to a ratchet 54 to advance ring gear 55 to rotate pinion 56 connected the effectors through a flexible cable 57 along axis 51. To reverse the direction of rotation switch 47 that turns rod 58 to shift to an alternate pinon 59 and reverse the rotation of the cable 57, see arrows in FIG. 23. Lever 60 as shown in FIG. 1 pivots the distal end 14 by linkage extending therethrough in a manner well known to those skilled in the art. The hollow tube 28 includes in an alternate a portal 38 in FIGS. 7 and 8 near the distal tip 18 for diverting the sensor 23 to a position to measure within the target tissue 11 the extent of ablation about the effector 17 due to the passage of radio frequency current through the target tissue 11.

The sensor 23 in a light based system includes a fiber optic 39 in FIG. 8 for target tissue 11 ablation measurement by changes in the radiation of the target tissue 11 with a radiation sensitive meter 40. The control 24 includes a radio frequency power modulator 41 to maintain the impedance at approximately its low point before it begins to rise. A user setting 42 in FIG. 19 is provided to set a predetermined value 43 of impedance and the control 24 includes a radio frequency power modulator 41 to maintain the impedance at the predetermined value 43. The power modulator 41 may be a voltage circuit such that the output of the RF or source 21 generator is proportional to the voltage out of the power modulator 41. The power modulator 41 may alternately be digital such that it gives a number proportional to power digitally to the RF generator or source 21 which then has a digital to analog converter to produce a voltage that is proportional to power output. The sensor 23 includes in an alternate based on temperature detection a probe 44 in FIG. 1 to find target tissue 11 temperature changes during the delivery of radio frequency current to the target tissue 11 and the control 24 examines the changes for a rise in temperature from a preset value 45. A look up table 46 is provided to supply at least one preset value 45 of temperature as a function of measured impedance and the control 24 includes a radio frequency power modulator 41 to maintain the temperature at the preset value 45. The preset value 45 of temperature is in the range of about 60 to 105 degrees Celsius. A ramp up in FIG. 20 curve of the temperature can also be stored on a lookup table 46 so the heatup of the tissue 11 follows the ramp.

End effector 17 could have a lumen 29 for fluid 30 to pass cooling fluid to cool, e.g., hollow tube 28 in FIG. 9. This could be a configuration such that the flow of cooling fluid enters the assembly through the lumen 29 and extends therethrough in the outer hollow tube 28 as shown in FIGS. 7 and 9. The lumens could be coaxially oriented as shown in FIG. 10 or split inner chamber as shown in FIG. 11.

The electrosurgical apparatus 10 adapted for ablating target tissue 11 has a switch 47 as seen in FIG. 1 for changing direction of the rotation of the effector 17 as the handpiece is squeezed between the two members 52 and 53. In addition, an activation lever 60 controls the angle of the distal end about the pivot point. This aids in the delivery of the device into myomas on various locations on the uterus.

The framework 33 on a hollow tube 28 is made of an electrically insulating material 26 and the electrodes 31 and 32 are preferable to a vapor deposition of conductive materials 48 in FIG. 5 and radio frequency current is supplied to the electrodes 31 and 32 has at least two polarities provided within or along the framework 33. The handle 12 carries an extending cylindrical support 49 in FIGS. 12,13 and 14 along the axis 51 for moving the effector 17 therewithin and a port 50 in FIGS. 12 and 14 through the extending cylindrical support 49 permits exit for the distal tip 18 so that upon the rotation of the effector 17 about its axis 16 the distal tip 18 adjoining the helical shape is screwed out of the extending cylindrical support 49 to place the helical shape within the target tissue 11 surrounding the extending cylindrical support 49.

A method of ablating subsurface target tissue 11 without ablating the surface tissue see FIGS. 16 and 17 where the surface is about the initial entry point of the effector 17 with its helical shape extending along its axis 16 and having the sharpened distal tip 18 for insertion and the source of radio frequency current 21 couples to the effector 17 so the sensor 23 measures within the target tissue 11 the extent of ablation about the effector 17 due to the passage of radio frequency current through the target tissue 11. The method has steps of inserting the distal tip 18 into the initial entry point, rotating the effector 17 about its axis 16 to screw the helical shape into the subsurface target tissue 11, and delivering controlled amounts of radio frequency current to the subsurface target tissue 11 to ablate the subsurface target tissue 11 while sparing the surface tissue from ablation.

The method includes the step of delivering controlled amounts of radio frequency current by measuring the impedance changes in the subsurface target tissue 11 about the distal tip 18 with a sensor 23 set to modulate the radio frequency current to achieve a preset impedance. The method has the step of delivering controlled amounts of radio frequency current by measuring the temperature changes in the subsurface target tissue 11 about the distal tip 18 with sensor 23 set to adjust the radio frequency current to a preset temperature.

Figure 25:
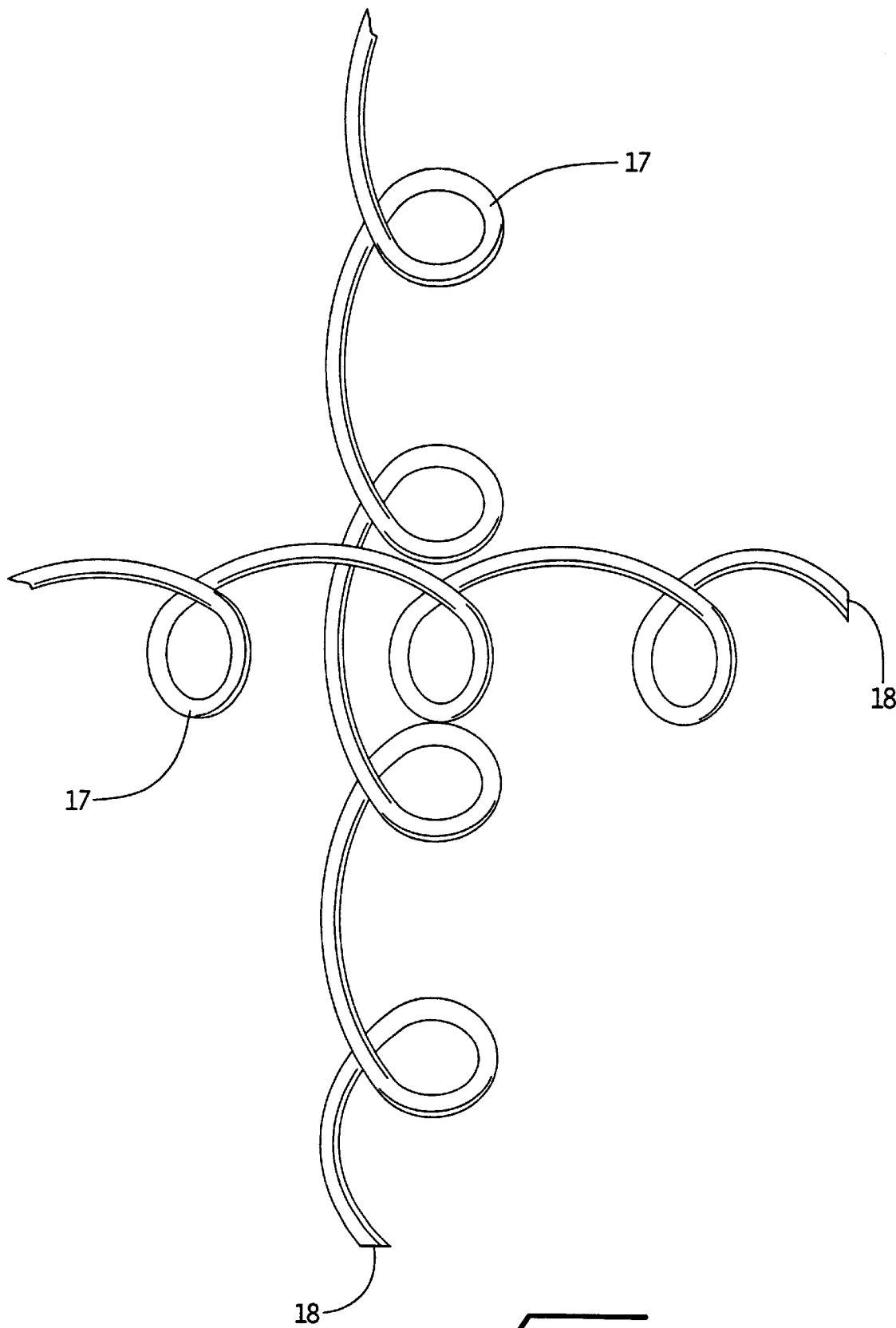
FIG. 25 is a view of two helical shaped effectors extending to their distal tips for use as electrodes and shown at an angle and their axes may even intersect although they might not touch.

The helical shape effector 17 is in an alternate composed of more than one helix 31 and 32 along the axis 16 in FIG. 6 for forming the effector and at least one distal tip 18 for entry into the tissue of each helix, so each helix is in the circuit with its return electrode 22. The helical shape is in another arrangement shown schematically in FIGS. 24 and 25 composed of more than one helix wherein one is along the axis and the other helics are spaced therefrom for forming the effector 17. At least one distal tip 18 for entry into the tissue 11 by each helix so the polarity of each helix could be different for bipolar delivery of radio frequency current therebetween and thereabout. The helical shape effector 17 is in a different form composed of more than one helix wherein one helix is along the axis and the other helices are spaced therefrom for forming the effector and at least one distal tip 18 for entry into the tissue of each helix, so each helix is in the circuit with its return electrode 22.

The helical shaped effector 17 of a study of goat mammary glands produced a lesion or ablation zone spherically shaped. The return electrode was on the goat's flank. The helical shaped effector 17 had a 16 mm diameter of 17 gage hollow stainless steel tubing with a 10 mm pitch between adjacent turns and with a 15 mm uninsulated active distal tip 17 similar to that shown in FIG. 3. The surface target tissue was spaced as the helical shaped effector 17 was insulated from the target tissue 11. An inner zone was necrosed and an outer zone was shell like surrounding the inner necrotic zone. A rim of hemorrhage (red in color) was apparent in the outer zone shell. Finally, a zone of edema surrounded the hemorrhage zone. The edema zone resolved itself in 3 days. The hemorrhagic zone resolved itself at 28 days and at that time the necrotic zone had nearly resolved itself and was no longer palpable. A small fibrotic mass was found in histologic analysis.

The prostate can also be treated through the urethra as shown in FIG. 13. The helical shape effector 17 is compressed in its delivery tube support 49 and then placed up through the penis and in the prostatic urethra, the helix is unwound through side exit port 50 as seen in FIG. 12 and placed into the tissue 11 of the prostate, on the outside of the delivery tube 49. This is also shown in FIG. 14.

Another embodiment is the helix placed transcrectally as shown in FIG. 15. If transcrectal, electrode insulation 26 may preferably be positioned so that both lobes of the prostate are heated by the active electrode 17 and so the urethra lying between them is not.

Preferably the helical shape effector 17 may be used to treat breast neoplasms, as in FIG. 16, wherein the target volume is centered within the helical shape effector 17 or around the outside thereof for the purpose of ablation. A 1.0 cm margin is treated around the neoplasm imaged by ultrasound, mammography, or magnetic resonance imaging. The return electrode 22 may also be placed around the breast, in a plane of the target volume. The return may also be placed elsewhere on the body. The neoplasm is heated and left in place to heal and fibrose. Subsequent imaging can show any further changes in the treated and target region.

The helical shape effector 17 may also be used to treat myomas or fibroids as shown in FIG. 17. The helix is insulated 26 near the entry point in order to spare the superficial tissue and minimize the formation of adhesions. The myoma is treated and no tissue removed. The myoma will initially shrink and then fibrose as part of the repair process.

The data measured and calculated during an ablation treatment is shown in FIG. 20. The target tissue 11 is heated from room temperature to 100° C. in the first 125 seconds. From this time until approximately 375 seconds, the temperature remains at 100° C. This temperature is measured along the central axis of the helix 16 in tissue 11, in the plane of the tip of the helix 18. Power remains between 38–40 Watts during the heatup period and is controlled to about 14 Watts to maintain the temperature at the 100° C. target. During the heatup, voltage is between 38 and 45 V and current is between 950 and 1020 mA. Note that impedance does not change. Carefully controlling power results in no impedance change, which if it increased would imply that the tissue 11 was excessively desiccated and would most likely adhere to the electrode and core out the tissue 11. This effect is undesirable and thus careful control of temperatures by controlling power results in a steady impedance value. Initially, impedance may fall, due to the relationship of tissue 11 temperature and impedance or conductivity as shown in FIG. 21.

FIG. 21 is a plot of conductivity of muscle target tissue 11 over time at a range of temperatures between 30 and 90 C. The conductivity of target tissue 11 is the inverse of the resistivity. The conductivity changes with increasing temperature and time. It is possible to measure the conductivity or resistivity of target tissue 11 at set temperatures and long time intervals. Laboratory tests show that if target tissue 11 is heated to a certain temperature and left at the temperature for a period of time, impedance measurements can be made at 500 kHz to characterize the target tissue 11 type. For example in muscle target tissue 11, if the target tissue 11 is heated to either 30, 40, 50 or 60 C. for 30 minutes, there is no impedance change over time. Each temperature endpoint will elicit a different conductivity, the conductivity being greater with increasing temperature. Resistivity will thus be less with increasing temperature. For samples that are heated to 60 C. or less, the conductivity did not change over time, once the target temperature was reached. For samples heated greater than 60 C., the samples decreased in conductivity over time. These measurements were made using bovine muscle target tissue. In addition, if the samples of target tissue are cooled back to their normal or baseline temperatures, the conductivity values will return to where they started, only if heated below 70 C. For the samples heated to 70 or 90 C., the conductivities do not return to baseline values, inferring irreversible changes in the target tissue.

Any number of orientations among two or more helices could be used. A pair of helices 17 is shown in FIG. 24. Any number of helices could be interconnected in this fashion. Another embodiment is found in FIG. 25 with an angled orientation between the pair of helices 17.

While a particular preferred embodiment has been illustrated and described the scope of protection sought is in the claims that follow.

What is claimed is:

1. An electrosurgical apparatus for thermally treating tissue, the apparatus comprising:

an elongate body having a proximal end and a distal end and defining a longitudinal axis;

an effector mounted to the distal end of the body and being rotatable relative to the body, the effector having a general helical shaped portion and having a sharpened distal closed tip, the effector having defining an internal lumen for circulating cooling fluid within the effector to cool the effector;

a source of cooling fluid in fluid communication with the internal lumen of the effector;

a drive member disposed within the elongate body and operatively connected to the effector, the drive member axially stationary relative to the elongate body and being rotatable to cause corresponding rotational movement of the effector;

a source of radio frequency current coupled to the effector and insulated from the body;

a sensor mounted to the distal end of the elongate body and extending within an inner boundary defined within the helical shaped portion to measure within the target tissue the extent of ablation about the effector due to the passage of radio frequency current through the target tissue;

a control coupled between the source of radio frequency current and the sensor to effect a loop regulation of the delivery of the radio frequency current for defining the extent of ablation; and an actuator operatively connected to the effector whereby manipulation of the actuator causes corresponding rotational movement of the drive member and the effector relative to the elongate body.

2. The electrosurgical apparatus according to claim 1 wherein the effector is an RF electrode having an insulating sleeve.

3. The electrosurgical apparatus according to claim 1 wherein a calculator is associated with the sensor to find impedance changes during the delivery of radio frequency current to the target tissue and the control examines the changes for a rise in impedance calculated.

4. The electrosurgical apparatus according to claim 3 wherein the control includes a radio frequency power modulator to maintain the impedance at approximately the low point before it begins to rise.

5. The electrosurgical apparatus according to claim 3 wherein a user setting is provided to set a predetermined value of impedance and the control includes a radio frequency power modulator to maintain the impedance at the predetermined value.

6. The electrosurgical apparatus according to claim 1 wherein the effector is a hollow tube bent into the helical shape and the elongate body includes a passage for fluid circulation within the hollow tube.

7. The electrosurgical apparatus according to claim 6 wherein the hollow tube includes a portal near the distal tip for diverting the sensor to a position to measure within the target tissue the extent of ablation about the effector due to the passage of radio frequency current through the target tissue.

8. The electrosurgical apparatus according to claim 1 wherein the sensor includes a fiber optic to quantify target tissue ablation measurement by changes in the radiation of the target tissue with a radiation sensitive meter.

9. The electrosurgical apparatus according to claim 1 wherein the sensor includes a probe to find target tissue temperature changes during the delivery of radio frequency current to the target tissue and the control examines the changes for a rise in temperature from a preset value.

10. The electrosurgical apparatus according to claim 9 wherein a look up table is provided to supply at least one preset value of temperature as a function of measured impedance and the control includes a radio frequency power modulator to maintain the temperature at the preset value.

11. The electrosurgical apparatus according to claim 9 wherein the preset value of temperature is in the range of about 60 to 105 degrees Celsius.

12. The electrosurgical apparatus according to claim 1 wherein the actuator is rotatable.

13. The electrosurgical apparatus according to claim 1 wherein the effector includes an outer wall which defines the internal lumen, the outer wall being devoid of openings.

14. A method of ablating subsurface target tissue without ablating surface tissue where the surface is about an initial entry point, the method comprising the steps of:

providing an electrosurgical apparatus, the apparatus including an elongate body defining a longitudinal axis, a drive member disposed within the elongate body and rotatable therewithin, and an effector mounted to the body and operatively connected to the drive member, the effector being rotatable upon rotational movement of the drive member, the effector having a general helical shaped portion and a sharpened distal tip and a source of radio frequency current coupled to the effector;

inserting the distal tip of the effector into the initial entry point;

rotating the drive member to cause rotational movement of the effector relative to the body such that the effector penetrates the subsurface target tissue without longitudinally moving the drive member relative to the elongate body; and delivering controlled amount of radio frequency current to the subsurface target tissue while sparing the surface tissue from ablation.

15. The method of claim 14 wherein the step of delivering controlled amounts of radiofrequency current includes measuring impedance changes in the subsurface target tissue about the subsurface target tissue about the distal tip with a sensor.

16. The method of claim 14 with the step of delivering controlled amounts of radio frequency current by measuring the temperature changes in the subsurface target tissue about the distal tip with a sensor set to adjust the radio frequency current to a preset temperature.

17. An electrosurgical apparatus for thermally treating tissue, the apparatus comprising:

an elongate body having a proximal end and a distal end and defining a longitudinal axis;

an electrode mounted to the elongate body and extending from the distal end of the body, the electrode having a generally helical configuration along at least a portion of its length and being rotatable relative to the elongate body, the electrode having an outer insulating sleeve mounted thereto and arranged to define at least two spaced exposed conductive portions of the electrode;

a source of radio frequency (RF) energy in electrical communication with the effector and being electrically insulated from the elongate body; and a handle mounted to the elongated body, the handle including a frame and an actuator pivotally mounted to the frame, the actuator operatively connected to the effector such that pivotal movement of the actuator causes corresponding rotational movement of the effector.

18. The apparatus according to claim 17, wherein the electrode has a sharpened tip at a distal end thereof for penetrating tissue.

19. The apparatus according to claim 18, wherein the electrode includes a monopolar RF electrode.

20. The apparatus according to claim 18, wherein the first-mentioned electrode is an active RF electrode and further including a second return electrode.

21. The apparatus according to claim 18, further comprising a sensor mounted to the elongate body and extending from the distal end of the elongate body to measure the extent of thermal treatment of the tissue.

22. The apparatus according to claim 21, wherein the sensor is adapted to measure an impedance value of the tissue during treatment, and further including a control to compare the measured impedance value to a preset impedance value whereby the control cooperates with the source of RF energy to maintain the measured impedance value of the tissue at the preset impedance value.

23. The apparatus according to claim 21, wherein the sensor is adapted to measure a temperature value of the tissue during treatment, and further including a control to compare the measured temperature value to a preset temperature value whereby the control cooperates with the source of RF energy to maintain the measured temperature value of the tissue at the preset temperature value.

24. The apparatus according to claim 21, wherein the sensor extends from the distal end of the body and is located within an interior area defined by the generally helical configuration of the electrode.

25. The apparatus according to claim 21, wherein the electrode defines an internal passageway for support of the sensor therewithin, the effector further defining a portal for positioning the sensor to measure the extent of thermal treatment of the tissue.

26. The apparatus according to claim 18, wherein at least two electrodes of opposite polarity are mounted to the elongate body.

27. The apparatus according to claim 18, wherein the electrode defines an internal passageway for fluid circulation therewithin.

28. The apparatus according to claim 27, wherein the body defines a passageway in fluid communication with the internal passageway of the electrode.

29. The apparatus according to claim 18, wherein a handle is mounted to the proximal end of the body, the handle including a rotation mechanism for causing rotation of the electrode.

30. The apparatus according to claim 29, wherein the rotation mechanism includes an actuator coupled to the handle and movable relative to the body to cause rotation of the electrode.

31. The apparatus according to claim 30, wherein the actuator is coupled to a ratchet mechanism for incremental rotation of the electrode.

32. The apparatus according to claim 30, wherein the handle further includes a lever for controlling rotational direction.

33. The apparatus according to claim 18, wherein the electrode is retractable within an internal passageway defined within the body.

34. An electrosurgical apparatus for thermally treating tissue, the apparatus comprising:

an elongate body having a proximal end and a distal end and defining a longitudinal axis;

an effector mounted to the elongate body and extending from the distal end of the elongate body, and being rotatable relative to the elongate body, the effector including at least two generally helical shaped monopolar RF electrodes, each RF electrode having a sharpened tip at a distal end thereof for penetrating tissue; and a source of radio frequency (RF) energy in electrical communication with the effector and being electrically insulated from the elongate body.

35. An electrosurgical apparatus for thermally treating tissue, the apparatus comprising:

an elongate body having a proximal end and a distal end and defining a longitudinal axis;

an articulating member mounted to the distal end of the elongate body, the articulating member adapted to pivot relative to the longitudinal axis of the body;

an effector mounted to the articulating member to pivot therewith, the effector having a generally helical configuration along at least a portion of its length and being rotatable relative to the articulating member; and a source of radio frequency (RF) energy in electrical communication with the effector and being electrically insulated from the elongate body.

36. A method for treating prostatic tissue, the method comprising the steps of:

providing an electrosurgical apparatus, the apparatus including an elongate body and at least one effector mounted to the body and extending from the distal end of the body, the effector having a generally helical configuration along at least a portion of its length and being rotatable relative to the body;

positioning the apparatus within a prostatic urethra;

rotating the effector relative to the body to cause penetration into the prostatic tissue; and supplying RF energy to the effector from and RF energy source to thermally treat the prostatic tissue.

37. The method according to claim 36, wherein the apparatus further includes a sensor and further including a step of measuring the extent of treatment.

38. The method according to claim 36, wherein the step of rotating includes moving a manually manipulable actuator operatively connected to the effector whereby manipulation of the actuator causes corresponding rotational movement of the effector.

39. The method according to claim 38 wherein the actuator is pivotally mounted with respect to the elongate body and wherein the step of rotating includes pivoting the actuator to cause rotational movement of the effector.

40. An electrosurgical apparatus for thermally treating tissue, which comprises:

an elongate body;

an effector mounted to the elongate body, the effector having a general helical coiled configuration along at least a portion of a length thereof, the effector having an outer wall defining an enclosed internal lumen for circulating cooling fluid through the effector; and an electromagnetic energy source in electrical communication with the effector.

41. The electrosurgical apparatus according to claim 40 wherein the electromagnetic energy source is a radio frequency source, the effector being a radio frequency electrode.

42. An electrosurgical apparatus for thermally treating tissue, which comprises:

an elongate body;

an effector mounted to the elongate body, the effector having a general helical coiled configuration along at least a portion of a length thereof, the effector including an internal lumen and having a portal in the outer wall in communication with the internal lumen;

a sensor probe disposed within the internal lumen of the effector to measure a degree of thermal treatment of tissue adjacent the effector, the sensor probe extendable through the portal of the effector; and an electromagnetic energy source in electrical communication with the effector.

* * * * *